United States Patent [19]

Davie et al.

[11] Patent Number: 4,994,371
[45] Date of Patent: Feb. 19, 1991

[54] DNA PREPARATION OF CHRISTMAS FACTOR AND USE OF DNA SEQUENCES

[76] Inventors: Earl W. Davie, 9010 N.E. 22nd Pl., Bellevue, Wash. 98004; Kotoku Kurachi, 4022 N.E. 104 Ave., Seattle, Wash. 98125

[21] Appl. No.: 355,900

[22] Filed: May 19, 1989

Related U.S. Application Data

[63] Continuation of Ser. No. 94,031, Aug. 28, 1987, abandoned, which is a continuation of Ser. No. 888,041, Jul. 18, 1986, abandoned, which is a continuation of Ser. No. 735,702, May 16, 1985, abandoned, which is a continuation of Ser. No. 437,009, Oct. 28, 1982, abandoned.

[51] Int. Cl.$^5$ .................... C12Q 1/68; C12N 15/12
[52] U.S. Cl. ............................ 435/6; 536/27; 435/320.1; 435/11; 435/172.3; 435/243; 935/1; 935/2; 935/6; 935/8; 935/9; 935/11; 935/12; 935/23; 935/29; 935/56; 935/62; 935/78; 935/80; 935/81; 436/501; 436/504
[58] Field of Search ..................... 536/27; 435/6, 320, 435/172.3

[56] References Cited

U.S. PATENT DOCUMENTS 4,497,796 2/1985 Salser .................................. 424/95

FOREIGN PATENT DOCUMENTS 2125409A 3/1984 United Kingdom .

OTHER PUBLICATIONS

Fujikawa, K. et al., (1973) Biochemistry, vol. 12: pp. 4938–4945, "Isolation and Characterization of Bovine Factor IX".
DiScipio, R. G. et al., (1977), Biochemistry, vol. 16: pp. 698–706, "A Comparison of Human Prothrombin, Factor IX (Christmas Factor Factor X (Stuart Factor), and Protein S".
Katayama, K. et al., (1979), Proc. Natl. Aca. Sci. USA, vol. 76: pp. 4990–4994, "Comparison of Amino Acid Sequence of Bovine Coagulation Factor IX (Christmas Factor) with that of other Vitamin K-Dependent Plasma Proteins".
DiScipio, R. G. et al., (1978), J. Clin. Invest., vol. 61: pp. 1528–1537, "Activation of Human Factor IX (Christmas Factor)".
Choo, K. H. et al., (1982), Nature, vol. 299: pp. 178–180, "Molecular Cloning of the Gene for Human Anti-Haemophilic Factor IX".
Wallace, R. B. et al. (1981), Nucleic Acids Research, vol. 9, pp. 879–894, "The Use of Synthetic Oligonucleotides as Hybridization Probes".
Fujikawa, K. et al. (1974), Biochemistry vol. 13: pp. 4508–4516, "The Mechanism of Activation of Bovine Factor IX (Christmas Factor) by Bovine Factor IXa (Activated Plasma Thromboplastin Antecedent)".
Hedner, U. and Davie, E. W. (1982) In: Hemostasis and Thrombosis, Colman, R. W., Hirsch, J., et al., eds., J. B. Lippincott Co., Philadelphia, Pa., pp. 29–38, "Factor IX".

Primary Examiner—Lester L. Lee
Assistant Examiner—Nina Ossanna
Attorney, Agent, or Firm—Seed and Berry

[57] ABSTRACT

There is disclosed an isolated DNA sequence and the amino acid sequence for human factor IX. The isolated DNA sequence and its flanking sequences are useful for determining mutations, deletions or other modifications in genetic sequences expressing normal factor IX or modifications thereof.

23 Claims, 5 Drawing Sheets

FIG. 1

```
              -45                              -40
         Met  Gln  Arg  Val  Asn  Met  Ile  Met  Ala
5'C(11) A T G C A G C G C G T G A A C A T G A T C A T G G C A
              20                 30

-35                              -30
         Glu  Ser  Pro  Ser  Leu  Ile  Thr  Ile  Cys  Leu
        G A A T C A C C A A G C C T C A T C A C C A T C T G C C T T
         40                 50                 60

-25                              -20
         Leu  Gly  Tyr  Leu  Leu  Ser  Ala  Glu  Cys  Thr
        T T A G G A T A T C T A C T C A G T G C T G A A T G T A C A
         70                 80                 90

-15                              -10
         Val  Phe  Leu  Asp  His  Glu  Asn  Ala  Asn  Lys
        G T T T T C T T G A T C A T G A A A A C G C C A A C A A A
         100                110                120

-5                               +1
         Ile  Leu  Asn  Arg  Pro  Lys  Arg  Tyr  Asn  Ser
        A T T C T G A A T C G G C C A A A G A G G T A T A A T T C A
         130                140                150

10
         Gly  Lys  Leu  Glu  Glu  Phe  Val  Gln  Gly  Asn
        G G T A A A T T G G A A G A G T T T G T T C A A G G G A A C
         160                170                180

20
         Leu  Glu  Arg  Glu  Cys  Met  Glu  Glu  Lys  Cys
        C T T G A G A G A G A A T G T A T G G A A G A A A A G T G T
         190                200                210

30
         Ser  Phe  Glu  Glu  Ala  Arg  Glu  Val  Phe  Glu
        A G T T T T G A A G A A G C A C G A G A A G T T T T T G A A
         220                230                240

40
         Asn  Thr  Glu  Lys  Thr  Thr  Glu  Phe  Trp  Lys
        A A C A C T G A A A A G A C A A C T G A A T T T T G G A A G
         250                260                270

50
         Gln  Tyr  Val  Asp  Gly  Asp  Gln  Cys  Glu  Ser
        C A G T A T G T T G A T G G A G A T C A G T G T G A G T C C
         280                290                300

60
         Asn  Pro  Cys  Leu  Asn  Gly  Gly  Ser  Cys  Lys
        A A T C C A T G T T T A A A T G G C G G C A G T T G C A A G
         310                320                330
```

```
                                              70
       Asp  Asp  Ile  Asn  Ser  Tyr  Glu  Cys  Trp  Cys
       G A T G A C A T T A A T T C C T A T G A A T G T T G G T G T
       340            350            360

80
       Pro  Phe  Gly  Phe  Glu  Gly  Lys  Asn  Cys  Glu
       C C C T T T G G A T T T G A A G G A A A G A A C T G T G A A
       370            380            390

90
       Leu  Asp  Val  Thr  Cys  Asn  Ile  Lys  Asn  Gly
       T T A G A T G T A A C A T G T A A C A T T A A G A A T G G C
       400            410            420

100
       Arg  Cys  Glu  Gln  Phe  Cys  Lys  Asn  Ser  Ala
       A G A T G C G A G C A G T T T T G T A A A A A T A G T G C T
       430            440            450

110
       Asp  Asn  Lys  Val  Val  Cys  Ser  Cys  Thr  Glu
       G A T A A C A A G G T G G T T T G C T C C T G T A C T G A G
       460            470            480

120
       Gly  Tyr  Arg  Leu  Ala  Glu  Asn  Gln  Lys  Ser
       G G A T A T C G A C T T G C A G A A A A C C A G A A G T C C
       490            500            510

130
       Cys  Glu  Pro  Ala  Val  Pro  Phe  Pro  Cys  Gly
       T G T G A A C C A G C A G T G C C A T T T C C A T G T G G A
       520            530            540

140
       Arg  Val  Ser  Val  Ser  Gln  Thr  Ser  Lys  Leu
       A G A G T T T C T G T T T C A C A A A C T T C T A A G C T C
       550            560            570

150
       Thr  Arg  Ala  Glu  Ala  Val  Phe  Pro  Asp  Val
       A C C C G T G C T G A G G C T G T T T T T C C T G A T G T G
       580            590            600

160
       Asp  Tyr  Val  Asn  Pro  Thr  Glu  Ala  Glu  Thr
       G A C T A T G T A A A T C C T A C T G A A G C T G A A A C C
       610            620            630

170
       Ile  Leu  Asp  Asn  Ile  Thr  Gln  Gly  Thr  Gln
       A T T T T G G A T A A C A T C A C T C A A G G C A C C C A A
       640            650            660
```

FIG. 1 CONT.

```
                                           180
  Ser  Phe  Asn  Asp  Phe  Thr  Arg  Val  Val  Gly
T C A T T T A A T G A C T T C A C T C G G G T T G T T G G T
670            680                690

190
  Gly  Glu  Asp  Ala  Lys  Pro  Gly  Gln  Phe  Pro
G G A G A A G A T G C C A A A C C A G G T C A A T T C C T
700            710                720

200
  Trp  Gln  Val  Val  Leu  Asn  Gly  Lys  Val  Asp
T G G C A G G T T G T T T T G A A T G G T A A A G T T G A T
730            740                750

210
  Ala  Phe  Cys  Gly  Gly  Ser  Ile  Val  Asn  Glu
G C A T T C T G T G G A G G C T C T A T C G T T A A T G A A
760            770                780

220
  Lys  Trp  Ile  Val  Thr  Ala  Ala  His  Cys  Val
A A A T G G A T T G T A A C T G C T G C C C A C T G T G T T
790            800                810

230
  Glu  Thr  Gly  Val  Lys  Ile  Thr  Val  Val  Ala
G A A C T G G T G T T A A A A T T A C A G T T G T C G C A
820            830                840

240
  Gly  Glu  His  Asn  Ile  Glu  Glu  Thr  Glu  His
G G T G A A C A T A A T A T T G A G G A G A C A G A A C A T
850            860                870

250
  Thr  Glu  Gln  Lys  Arg  Asn  Val  Ile  Arg  Ala
A C A G A G C A A A A G C G A A A T G T G A T T C G A G C A
880            890                900

260
  Ile  Ile  Pro  His  His  Asn  Tyr  Asn  Ala  Ala
A T T A T T C C T C A C C A C A A C T A C A A T G C A G C T
910            920                930

270
  Ile  Asn  Lys  Tyr  Asn  His  Asp  Ile  Ala  Leu
A T T A A T A A G T A C A A C C A T G A C A T T G C C C T T
940            950                960

280
  Leu  Glu  Leu  Asp  Glu  Pro  Leu  Val  Leu  Asn
C T G G A A C T G G A C G A A C C C T T A G T G C T A A A C
970            980                990
```

FIG. 1 CONT.

```
                                        290
    Ser   Tyr   Val   Thr   Pro   Ile   Cys   Ile   Ala   Asp
    A G C T A C G T T A C A C C T A T T T G C A T T G C T G A C
   1000             1010              1020

300
    Lys   Glu   Tyr   Thr   Asn   Ile   Phe   Leu   Lys   Phe
    A A G G A A T A C A C G A A C A T C T T C C T C A A A T T T
   1030             1040              1050

310
    Gly   Ser   Gly   Tyr   Val   Ser   Gly   Trp   Gly   Arg
    G G A T C T G G C T A T G T A A G T G G C T G G G G A A G A
   1060             1070              1080

320
    Val   Phe   His   Lys   Gly   Arg   Ser   Ala   Leu   Val
    G T C T T C C A C A A A G G G A G A T C A G C T T T A G T T
   1090             1100              1110

330
    Leu   Gln   Tyr   Leu   Arg   Val   Pro   Leu   Val   Asp
    C T T C A G T A C C T T A G A G T T C C A C T T G T T G A C
   1120             1130              1140

340
    Arg   Ala   Thr   Cys   Leu   Arg   Ser   Thr   Lys   Phe
    C G A G C C A C A T G T C T T C G A T C T A C A A A G T T C
   1150             1160              1170

350
    Thr   Ile   Tyr   Asn   Asn   Met   Phe   Cys   Ala   Gly
    A C C A T C T A T A A C A A C A T G T T C T G T G C T G G C
   1180             1190              1200

360
    Phe   His   Glu   Gly   Gly   Arg   Asp   Ser   Cys   Gln
    T T C C A T G A A G G A G G T A G A G A T T C A T G T C A A
   1210             1220              1230

370
    Gly   Asp   Ser   Gly   Gly   Pro   His   Val   Thr   Glu
    G G A G A T A G T G G G G G A C C C C A T G T T A C T G A A
   1240             1250              1260

380
    Val   Glu   Gly   Thr   Ser   Phe   Leu   Thr   Gly   Ile
    G T G G A A G G G A C C A G T T T C T T A A C T G G A A T T
   1270             1280              1290

390
    Ile   Ser   Trp   Gly   Glu   Glu   Cys   Ala   Met   Lys
    A T T A G C T G G G G T G A A G A G T G T G C A A T G A A A
   1300             1310              1320
```

FIG. 1 CONT.

```
         Gly   Lys   Tyr   Gly   Ile   Tyr   Thr   Lys   Val   Ser
       G G C A A A T A T G G A A T A T A T A C C A A G G T A T C C
       1330              1340               1350
                                           410
         Arg   Tyr   Val   Asn   Trp   Ile   Lys   Glu   Lys   Thr
       C G G T A T G T C A A C T G A T T A A G G A A A A A A C A
       1360              1370               1380
                     416
         Lys   Leu   Thr   STOP
       A A G C T C A C T T A A T G A A G A T G G A T T T C C A A
       1390              1400               1410

DNA PREPARATION OF CHRISTMAS FACTOR AND USE OF DNA SEQUENCES

This invention was made in part with government support under Grants RR 00166 and HL 15919 from the National Institutes of Health. The United States Government may claim an interest in this invention.

This application is a continuation of U.S. application Ser. No. 07/094,031 filed Aug. 28, 1987, now abandoned, which is a continuation of U.S. Pat. application Ser. No. 888,041, filed July 18, 1986, now abandoned, which is a continuation of U.S. Pat. application Ser. No. 735,702, filed May 16, 1985, now abandoned, which is a continuation of U.S. Pat. application Ser. No. 437,009, filed Oct. 28, 1982, now abandoned.

BACKGROUND OF THE INVENTION

1. Field of the Invention

Factor IX (Christmas factor) is a vitamin K-dependent plasma protein that plays an important role in the middle phase of blood coagulation. Individuals lacking this protein may bleed spontaneously into their skin, soft tissues and joints. This bleeding is often serious in patients even after a minor injury. A deficiency of factor IX (Christmas disease or hemophilia B) affects males primarily, since it is transmitted as a sex-linked recessive trait. The human and bovine proteins contain 12 $\gamma$-carboxyglutamic acid residues in their amino-terminal regions. During the coagulation process, factor IX is converted to factor $IX_a$ (a serine protease) by factor $XI_a$, Fujikawa et al., *Biochemistry* (1974) 13:4508–4516. This factor then reacts with factor X and by successive steps coagulation occurs.

The amount of factor IX is extremely small and only difficultly obtainable. There is, therefore, difficulty in either obtaining the genetic information from the chromosome or preparing sufficient messenger RNA for successful reverse transcription of a complete sequence for factor IX.

2. Description of the Prior Art

Factor IX has been extensively purified from bovine and human plasma, as described by Fujikawa et al., *Biochemistry* (1973) 12:4938–4945 and DiScipio et al., ibid. (1977) 16:698–706. Approximately 20% of the amino acid sequence for the human molecule has been determined, DiScipio et al., *J. Clin. Invest.* (1978) 61:1528–1538. The entire sequence for the bovine molecule has been established. Katayama et al., *PNAS USA* (1979) 76:4990–4994. Both proteins are single-chain glycoproteins ($M_r$, 55,000– 57,000) with an amino-terminal sequence of Y-N-S-G-K. Choo et al., *Nature* (1982) 299:178–180, describe the partial characterization of the human factor IX gene.

SUMMARY OF THE INVENTION

Genetic sequences are provided capable of hybridizing to human factor IX, as well as flanking sequences of the human factor IX gene. The sequences can be labeled and can be used for determining mutations, deletions or other modifications in genetic sequences expressing normal human factor IX or modifications thereof. The DNA fragment may also be used in hybrid DNA technology for expression of polypeptides.

BRIEF DESCRIPTION OF THE DRAWING

The FIGURE is the sequence for factor IX as included in pHflxl. The nucleotide sequence of the coding strand and the corresponding predicted amino acid sequence are shown. The two arginyl peptide bonds (residues 145 and 180), cleaved during activation of factor IX are shown by the heavy arrows.

DESCRIPTION OF SPECIFIC EMBODIMENTS

DNA sequences are provided capable of binding to portions or all of the gene expressing human factor IX and flanking regions thereof. The sequences can be used in hybridization techniques for detecting genetic deficiencies and mutations involving human factor IX. By employing hybrid DNA technology, the sequences can be used for the production of polypeptides. The DNA sequences can be obtained free of introns, providing a continuous sequence coding for factor IX, precursors to factor IX or fragments of factor IX and their precursors. Also, the DNA sequences may include the sequences flanking the gene expressing human factor IX by themselves or in combination with human factor IX.

The polynucleotide sequences include the chromosomal gene, mRNA which has been matured and is capped and includes a poly(A) 3' chain, cDNA obtained by reverse transcription of fragments of any of the above, where the polynucleotide can be used for hybridization or for expression of a polypeptide having the sequence of all or part of factor IX. Also, mRNA, the combination of DNA sequences coding for a part or all of human factor IX may be joined to a vector for cloning, i.e. replication, or a plasmid provided including regulatory signals for expression, amplification and regulated response to a variety of conditions and reagents.

The nucleic acid sequences are sequences which will homoduplex or heteroduplex to the natural or mutated gene for human factor IX. The sequences may involve either RNA or DNA and will usually be at least about 14 bases long, more usually at least about 18 bases long and may be 3000 bases or longer. Where the fragments are to be used for hybridization, they will generally have fewer than about 1500 bases, usually be fewer than 1200 bases. For hybridization, the fragments may be labeled with a wide variety of labels, such as radionuclides e.g. $^{32}P$, haptens e.g. biotin, fluorescers, and the like. Various techniques may be employed for determining the occurrence of homo- or heteroduplexing, such as the Grunstein and Hogness technique (*PNAS USA* (1975) 72:3961–3965), the Southern technique (*J. Mol. Biol.* (1975) 98:503), the Northern technique (U.S. Pat. No. 4,302,204), or the like.

For determining the presence of sequences complementary to sequences encoding the factor IX gene, antibodies may be used which detect double-strandedness of DNA, RNA or a hybrid complex. The cellular polynucleotide to be assayed may be bound to a solid support, e.g. cellulose or nitrocellulose, by conventional means, e.g. heat, covalent diazo linkage, etc., or determined in solution, where a method is provided for detecting the formation of duplexes. The particular mode which is used for detecting the presence of duplexes is not a critical aspect of this invention, the subject invention providing the nucleotide sequences for human factor IX.

The polynucleotide sequences provided in accordance with this invention may be used in a variety of ways. The polynucleotide sequence may include the entire gene or the pseudogene (cDNA), including leader and prosequences and flanking regions. Fragments of the polynucleotide sequence may be taken, such sequences coding for factor IX; sequences coding for either the short or long chain of factor $IX_a$, factor $IX_{a\alpha}$ or factor $IX_{a\beta}$; sequences coding for the activation peptide; sequences coding for a polypeptide at the N-terminus involved in processing of factor IX; fragments of such sequences or combinations thereof.

It is found that while factor $IX_a$ is strongly conserved as evidenced by the sequences of bovine and human factor IX, the activation peptide has over time been subject to variation and there is substantial variation between the activation peptide involved with human factor IX and the activation peptide involved with bovine factor IX, while factor $IX_a$ in the two cases is substantially conserved.

The following is the complete sequence for factor IX as included in pHfIX1 (to be described subsequently).

```
              -45                    -40                    -35                    -30
       Met  Gln  Arg  Val  Asn  Met  Ile  Met  Ala  Glu  Ser  Pro  Ser  Leu  Ile  Thr  Ile  Cys  Leu  Leu  Gly
5' G(1) ATG  CAG  CGC  GTG  AAC  ATG  ATC  ATG  GCA  GAA  TCA  CCA  AGC  CTC  ATC  ACC  ATC  TGC  CTT  TTA  GCA
              20                     30                     40                     50                     60                     70

-25                    -20                    -15                    -10                     -5
       Tyr  Leu  Leu  Ser  Ala  Glu  Cys  Thr  Val  Phe  Leu  Asp  His  Glu  Asn  Ala  Asn  Lys  Ile  Leu  Asn  Arg  Pro
       TAT  CTA  CTC  AGT  GCT  GAA  TGT  ACA  GTT  TTT  CTT  GAT  CAT  GAA  AAC  GCC  AAC  AAA  ATT  CTG  AAT  CGG  CCA
              80                     90                    100                    110                    120                    130                    140

+1                                                         10                                                        20
       Lys  Arg  Tyr  Asn  Ser  Gly  Lys  Leu  Glu  Glu  Phe  Val  Gln  Gly  Asn  Leu  Glu  Arg  Glu  Cys  Met  Glu
       AAG  AGG  TAT  AAT  TCA  GGT  AAA  TTG  GAA  GAG  TTT  GTT  CAA  GGG  AAC  CTT  GAG  ACA  GAA  TGT  ATG  GAA
              150                    160                    170                    180                    190                    200                    210

30                                                         40
       Glu  Lys  Cys  Ser  Phe  Glu  Glu  Ala  Arg  Glu  Val  Phe  Glu  Asn  Thr  Glu  Lys  Thr  Thr  Glu  Phe  Trp
       GAA  AAG  TGT  AGT  TTT  GAA  GAA  GCA  CGA  GAA  GTT  TTT  GAA  AAC  ACT  GAA  AAG  ACA  ACT  CAA  TTT  TGC
              220                    230                    240                    250                    260                    270

50                                                         60
       Lys  Gln  Tyr  Val  Asp  Gly  Asp  Gln  Cys  Glu  Ser  Asn  Pro  Cys  Leu  Asn  Gly  Gly  Ser  Cys  Lys  Asp
       AAG  CAG  TAT  GTT  GAT  GGA  GAT  CAG  TGT  CAG  TCC  AAT  CCA  TGT  TTA  AAT  GGC  GGC  AGT  TGC  AAG  GAT
              280                    290                    300                    310                    320                    330                    340

70                                                         80
       Asp  Ile  Asn  Ser  Tyr  Glu  Cys  Trp  Cys  Pro  Phe  Gly  Phe  Glu  Gly  Lys  Asn  Cys  Glu  Leu  Asp  Val
       GAC  ATT  AAT  TCC  TAT  GAA  TCT  TGG  TGT  CCC  TTT  GGA  TTT  GAA  GGA  AAG  AAC  TGT  GAA  TTA  GAT  GTA
              350                    360                    370                    380                    390                    400

90                                                        100
       Thr  Cys  Asn  Ile  Lys  Asn  Gly  Arg  Cys  Glu  Gln  Phe  Cys  Lys  Asn  Ser  Ala  Asp  Asn  Lys  Val  Val
       ACA  TGT  AAC  ATT  AAG  AAT  GGC  AGA  TGC  GAG  CAG  TTT  TGT  AAA  AAT  AGT  GCT  GAT  AAC  AAG  GTG  GTT
              410                    420                    430                    440                    450                    460                    470

110                                                        120                                                       130
       Cys  Ser  Cys  Thr  Glu  Gly  Tyr  Arg  Leu  Ala  Glu  Asn  Gln  Lys  Ser  Cys  Glu  Pro  Ala  Val  Pro  Phe
       TGC  TCC  TGT  ACT  GAG  GGA  TAT  CGA  CTT  GCA  GAA  AAC  CAG  AAG  TCC  TCT  GAA  CCA  GCA  GTC  CCA  TTT
              480                    490                    500                                    520                    530                    540

140                                                        150
       Pro  Cys  Gly  Arg  Val  Ser  Val  Ser  Gln  Thr  Ser  Lys  Leu  Thr  Arg  Ala  Glu  Ala  Val  Phe  Pro  Asp  Val
       CCA  TGT  GGA  ACA  GTT  TCT  GTT  TCA  CAA  ACT  TCT  AAG  CTC  ACC  CGT  GCT  GAG  GCT  GTT  TTT  CCT  GAT  GTG
              550                    560                    570                    580                    590                    600

160                                                        170
       Asp  Tyr  Val  Asn  Pro  Thr  Glu  Ala  Glu  Thr  Ile  Leu  Asp  Asn  Ile  Thr  Gln  Gly  Thr  Gln  Ser  Phe
       GAC  TAT  GTA  AAT  CCT  ACT  GAA  GCT  GAA  ACC  ATT  TTG  GAT  AAC  ATC  ACT  CAA  GGC  ACC  CAA  TCA  TTT
       610                    620                    630                    640                    650                    660                    670

180                                                        190
       Asn  Asp  Phe  Thr  Arg  Val  Val  Gly  Gly  Glu  Asp  Ala  Lys  Pro  Gly  Gln  Phe  Pro  Trp  Gln  Val  Val
       AAT  GAC  TTC  ACT  CGG  GTT  GTT  GGT  GGA  GAA  GAT  GCC  AAA  CCA  GGT  CAA  TTC  CCT  TGG  CAG  GTT  GTT
              680                    690                    700                    710                    720                    730                    740

200                                                        210
       Leu  Asn  Gly  Lys  Val  Asp  Ala  Phe  Cys  Gly  Gly  Ser  Ile  Val  Asn  Glu  Lys  Trp  Ile  Val  Thr  Ala
       TTG  AAT  GGT  AAA  GTT  GAT  GCA  TTC  TGT  GGA  GGC  TCT  ATC  GTT  AAT  GAA  AAA  TGG  ATT  CTA  ACT  GCT
              750                    760                    770                    780                    790                    800

220                                   230                                                        240
       Ala  His  Cys  Val  Glu  Thr  Gly  Val  Lys  Ile  Thr  Val  Val  Ala  Gly  Glu  His  Asn  Ile  Glu  Glu  Thr
       GCC  CAC  TGT  GTT  GAA  ACT  GGT  GTT  AAA  ATT  ACA  GTT  GTC  GCA  GCT  GAA  CAT  AAT  ATT  GAG  GAG  ACA
              810                    820                    830                    840                    850                    860                    870
```

-continued

```
                                250                                                           260
Glu His Thr Glu Gln Lys Arg Asn Val Ile Arg Ala Ile Ile Pro His His Asn Tyr Asn Ala Ala
GAA CAT ACA GAG CAA AAG CGA AAT GTG ATT CGA GCA ATT ATT CCT CAC CAC AAC TAC AAT GCA GCT
            880         890         900         910         920         930

270                                         280
Ile Asn Lys Tyr Asn His Asp Ile Ala Leu Leu Glu Leu Asp Glu Pro Leu Val Leu Asn Ser Tyr
ATT AAT AAG TAC AAC CAT CAC ATT GCC CTT CTG GAA CTG GAC GAA CCC TTA GTG CTA AAC AGC TAC
940         950         960         970         980         990         1000

290                                     300
Val Thr Pro Ile Cys Ile Ala Asp Lys Glu Tyr Thr Asn Ile Phe Leu Lys Phe Gly Ser Gly Tyr
GTT ACA CCT ATT TGC ATT GCT GAC AAG GAA TAC ACG AAC ATC TTC CTC AAA TTT GGA TCT GGC TAT
    1010        1020        1030        1040        1050        1060        1070

310                                         320
Val Ser Gly Trp Gly Arg Val Phe His Lys Gly Arg Ser Ala Leu Val Leu Gln Tyr Leu Arg Val
GTA AGT GGC TGG GGA AGA GTC TTC CAC AAA GGG AGA TCA GCT TTA GTT CTT CAG TAC CTT AGA GTT
        1080        1090        1100        1110        1120        1130

330                                 340                                             350
Pro Leu Val Asp Arg Ala Thr Cys Leu Arg Ser Thr Lys Phe Thr Ile Tyr Asn Asn Met Phe Cys Ala
CCA CTT GTT GAC CGA GCC ACA TCT CTT CGA TCT ACA AAG TTC AAC ATC TAT AAC AAC ATG TTC TGT GCT
    1140        1150        1160        1170        1180        1190        1200

360                                         370
Gly Phe His Glu Gly Gly Arg Asp Ser Cys Gln Gly Asp Ser Gly Gly Pro His Val Thr Glu Val
GGC TTC CAT GAA GGA GGT AGA GAT TCA TGT CAA GGA GAT AGT GGG GGA CCC CAT GTT ACT GAA GTG
    1210        1220        1230        1240        1250        1260        1270

380                                     390
Glu Gly Thr Ser Phe Leu Thr Gly Ile Ile Ser Trp Gly Glu Glu Cys Ala Met Lys Gly Lys Tyr
GAA GGG ACC AGT TTC TTA ACT GGA ATT ATT AGC TGG GGT GAA GAG TGT GCA ATG AAA GGC AAA TAT
    1280        1290        1300        1310        1320        1330

400                                 410                             416
Gly Ile Tyr Thr Lys Val Ser Arg Tyr Val Asn Trp Ile Lys Glu Lys Thr Lys Leu Thr STOP
GGA ATA TAT ACC AAG GTA TCC CGG TAT GTC AAC TGG ATT AAG GAA AAA ACA AAG CTC ACT TAA TGAAA
1340        1350        1360        1370        1380        1390        1400

GATGGATTTCCAAGGTTAATTCATTGGAATTGAAAATTAACAGCCCCCCCCCCCCCCCCC
1410        1420        1430        1440        1450        1460        3'
```

The nucleotide sequence of the coding strand and the corresponding predicted amino acid sequence are shown. The coding strand is inserted and numbered in the same orientation as the ampicillin resistance gene of pBR322. The amino acid sequence corresponding to the entire mature protein is numbered 1–416. The amino acid sequence that corresponds to the leader sequence is represented by minus numbers in the opposite direction. The two arginyl peptide bonds (residues 145 and 180) cleaved during the activation of factor IX are shown by the heavy arrows.

The genetic information for factor IX may be obtained as follows: A primate is injected with antibodies to factor IX, so as to reduce the circulating level of factor IX to substantially below normal. The primate is then sacrificed and the liver rapidly removed. Poly(A)-containing mRNA is isolated and assayed for factor IX with reticulocyte lysate with specific immunoprecipitation of radiolabeled product. By employing the above technique, a multifold enhancement of mRNA level for factor IX is achieved.

The mRNA for factor IX is further enriched by specific immunoprecipitation of liver polysomes with antibodies to human factor IX. The mRNA may then be used to synthesize cDNA employing reverse transcriptase and an appropriate primer e.g. oligo(dT).

Alternatively, by having one or more probes based on a known amino acid sequence, where the probes are at least about 12 bases, preferably at least about 15 bases, a genetic library may be screened for the presence of the desired genetic information. The genetic library may be derived from sheared or restricted genome or from cDNA. Particularly, a human liver cDNA library may be employed. The recombinant plasmids which bind strongly to the probe are isolated and purified by conventional means e.g. cesium chloride gradient centrifugation, and the plasmids digested with an appropriate restriction endonuclease to excise the desired genetic information.

The DNA sequences will then be characterized in a number of ways. One characterization is restriction endonuclease mapping. Another characterization is the nucleotide sequence which may be determined in accordance with conventional ways. The sequence may then be cloned to provide for substantial amounts of the DNA sequences. In addition, the amino acid sequence may be determined from the nucleotide sequence.

The cDNA obtained from the liver cDNA library coding for human factor IX contained 1466 base pairs and is flanked by G-C tails of 11 and 18 base pairs at the 5' and 3' ends, respectively, the tails having been introduced for cohesion and annealing. Nucleotides 12 through 149 correspond to a leader sequence of 46 amino acids. The leader sequence contains three potential methionine start sites located at positions -46, -41 and -39. The methionine residues are then followed by a charged amino acid(s) (Arg at a position -45 or Glu at position -37) and a hydrophobic region rich in leucine, isoleucine, and tyrosine. These residues are typical of signal sequences found in most secreted proteins (Blobel et al. (1979) in Soc. for Experimental Biology Symp. XXXIII, *Secretory Mechanisms*, eds. Hopkins, C. R. & Duncan, C. J. (Cambridge University Press, Great Britain), pp. 9-36). These residues occur just prior to the Y—N—S—G—K sequence which is the amino-terminal sequence of the mature protein circulating in plasma.

Since the R—Y bond is not a typical cleavage site for signal peptidase, it appears likely that the newly synthesized factor IX in liver contains a pro-leader sequence analogous to serum albumin. This suggests that a signal peptidase cleaves at a peptide bond further upstream from the R—Y sequence, such as the A-N sequence (positions -10 and -9), the A-Q sequence (positions -21 and -20), or the S-A sequence (positions -22 and -21).

The mature protein for human factor IX is coded by 1248 pairs (nucleotides 150 through 1397) and is followed by a pair of adjacent stop codons of TAA and TGA. The molecular weight for the protein free of carbohydrate is calculated at 47,079. This is equivalent to a molecular weight of 56,722 upon the addition of 17% carbohydrate (DiScipio et al. (1978), supra). Human factor IX contains 12 glutamic acid residues in the amino-terminal region of the protein that are present as γ-carboxyglutamic acid (Gla) in the mature molecule. These residues are located at positions 7, 8, 15, 17, 20, 21, 26, 27, 30, 33, 36 and 40. The two internal peptide bonds hydrolyzed by factor XI$_a$ during the activation reaction are Arg$^{145}$ and Arg$^{180}$-Val$^{181}$. Cleavage of these two arginyl peptide bonds results in the formation of factor IX$_a$ (M$_r$, 43,196), a serine protease composed of a light chain (145 amino acids) and a heavy chain (236 amino acids) joined by disulfide links. The activation peptide (35 amino acids) is composed of residues 146 through 180 and includes four aspartic acid residues, three glutamic acid residues, one arginyl residue and probably modified with a plurality of sialic acid residues. The heavy chain contains the three principle residues involved in the catalytic activity of this serine protease, specifically His$^{221}$, Asp$^{270}$ and Ser$^{366}$.

The synthetic probe that was employed in the screening for the human factor IX plasmid was a nucleotide mixture that included a base sequence of TATTTGCCTTTCAT, which codes for the M—K—G—K—Y sequence in factor IX starting with Met$^{392}$. This amino acid sequence is present in both human and bovine factor IX. There are 69 changes in amino acid sequence between human and bovine proteins (Katayama et al. (1979), supra). There is in addition one insertion in bovine (Lys$^{143}$) and one deletion in bovine (Asn$^{259}$) factor IX. Both proteins contain 22 Cys residues which are present in the same positions in each protein. The largest difference in sequence between the two proteins occurs in the activation peptide where 17 of 35 residues have been changed. The overall identity between human and bovine factor IX was 83%.

The following examples are offered by way of illustration and not by way of limitation.

EXPERIMENTAL

MATERIALS AND METHODS

Preparation of Probes for Screening the cDNA Library

Two different radiolabeled DNA probes were employed in these experiments. One probe was prepared from baboon liver mRNA that was enriched for factor IX by the following procedures: A young male baboon (5 kilograms body weight) was injected over a period of 48 hours with a total of 73 mg of affinity-purified goat antibodies to human factor IX. This procedure reduced the circulating factor IX clotting activity level to less than 1% of normal. The baboon was then sacrificed and the liver rapidly removed and frozen in liquid nitrogen. Poly(A)-containing RNA was isolated (MacGillivray et al., *PNAS USA* (1980) 77:5153-5157) and assayed for factor IX with a rabbit reticulocyte lysate (Delham and Jackson, *Eur. J. Biochem.* (1976) 67:247-256) by specific immunoprecipitation of the radiolabeled product (MacGillivray et al., ibid. (1979) 98:477-485). By this assay, the liver mRNA level for factor IX was elevated approximately 5-fold when compared with a control animal. The mRNA for factor IX was enriched another 20-fold by specific immunoprecipitation of the liver polysomes with affinity-purified goat antibodies to human factor IX employing the procedure of Gough & Adams, *Biochemistry* (1978) 17:5560-5566. The final factor IX mRNA.-level was approximately 2% of the total as estimated by the reticulocyte translation assay. This mRNA was then used to synthesize a radiolabeled cDNA in the presence of dATP, dGTP, [α-$^{32}$P]dCTP, [α-$^{32}$P]TTP, reverse transcriptase, and oligo(dT) as primer (Stein et al., *Biochemistry* (1978) 17:5763-5772). The specific activity of the cDNA was 5×10$^7$ cpm/μg.

The second probe was a synthetic DNA mixture of 14 nucleotides in length and contained 12 different DNA sequences. These sequences were complementary to the amino acid sequence of Met-Lys-Gly-Lys-Tyr. The DNA mixture contained the following sequences:

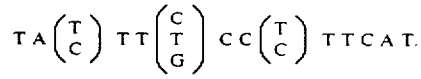

The DNA mixture was radiolabeled with T4 kinase and [γ-$^{32}$P]ATP to yield a specific activity of approximately 4×10$^8$ cpm/μg (Stein et al., (1978) supra). (Synthetic DNA mixture, P-L Biochemicals, Inc., Milwaukee, Wis.; T4 kinase, Bethesda Research Laboratories, Inc., Gaithersburg, Md.). Approximately 18,000 transformants were screened by a modification of the method of Wallace et al., (*Nucleic Acids Res.* (1981) 9:879-894).

The modified procedure was as follows: Colonies were grown on tetracycline (12.5 μg/mL) plates overnight at 37° C. (colony size 2-3 mm dia.) and the resulting colonies transferred to Whatman 540 filter paper (826 mm dia.). The filters with colonies up were placed onto chloramphenicol (250 μg/mL) plates, incubated overnight at 37° C. and then dried briefly in air (about 5 min.)

Lysis of the colonies was achieved by placing the filters with colonies up on the Whatman 3 mm paper wetted with 0.5N sodium hydroxide, the filters allowed to stand for 10 min. followed by blotting with clean white diaper cloth. The foregoing procedure was repeated, followed by transferring the filters onto the Whatman 3 mm paper wetted with 0.5M Tris, pH 7.4, the filters allowed to stand for 10 min., followed by blotting with diaper cloth and the procedure repeated. The filters were then transferred onto Whatman 3 mm paper, wetted with 2×SSC (1×SSC=0.15M NaCl, 0.015M sodium citrate, pH 7.0), the mixture allowed to stand for 10 min., blotted as before and the procedure repeated. After washing the filters briefly in 95% ethanol in a glass tray, the filters were air-dried for 20 min. and then either heated at 80° for 2 hours or 68° for several hours.

Hybridization was achieved by initially prehybridizing in 6×NET (1×NET=0.15M NaCl, 0.015M Tris- HCl, pH 7.5, 1 mM EDTA), 0.5% NP40 (Shell Oil Co.), 100 μg/mL yeast tRNA, for 2 hours at 55°. (*E. coli* DNA can be used to replace the yeast tRNA.) After briefly air-drying for about 5-10 minutes, hybridization was performed in 6×NET, 0.5% NP40, 250 μg/mL yeast tRNA and about 6-8 ng/mL labeled oligonucleotide at 35° for 15-20 hours. At the end of this time, the filters were washed at 0° C. with 4 changes of 6×SSC (250 mL) and then at 35° with two changes of 6×SSC for 10 min. The filters were then dried by blotting and exposed to X-ray film with an intensifier screen for 1-5 hours.

The human liver cDNA library (S.L.C. Woo and C. Thirumalachary) contained cDNA inserted into the Pst I site of plasmid pBR322. Four recombinant plasmids that hybridized strongly with the probe were isolated and purified by cesium chloride gradient centrifugation. DNA samples of the positive clone were then digested with Pst I, and the resulting fragments were analyzed by polyacrylamide gel electrophoresis. These inserts were also mapped by restriction endonucleases (Bethesda Research Laboratories, Inc., Gaithersburg, Md.).

DNA Sequence Analysis

Restriction fragments were labeled at the 3' end with [$\alpha$-$^{32}$P] cordycepin 5'-phosphate in the presence of terminal deoxynucleotide transferase under conditions specified by the manufacturer (New England Nuclear, Boston, Mass.). They were also labeled at the 5' end with [$\gamma$-$^{32}$P]ATP in the presence of T4 kinase after prior treatment of the DNA with bacterial alkaline phosphatase (Worthington Biochemical Co., Freehold, N.J.) or by an exchange reaction of the 5' phosphate group of [$\gamma$-$^{32}$O]ATP in the presence of T4 kinase (Maxam and Gilbert, *Methods Enxymol.* (1980) 65:499-560). Labeled fragments were then subjected to base modification and cleavage as described by Maxam and Gilbert, ibid., and subjected to electrophoresis on 0.35 mm polyacrylamide gels containing 8.3 M urea. The majority (92%) of the nucleotide sequence was established by two or more sequence experiments, and approximately 80% was determined on both strands.

Four positive clones were identified from a human liver cDNA library of 18,000 recombinant plasmids employing the synthetic oligonucleotide mixture described above and a single-stranded DNA prepared from enriched mRNA for baboon factor IX as probes. With two of these plasmids, the cDNA was readily released by digestion with Pst I, yielding an insert of approximately 1500 base pairs. In preliminary experiments, these two clones were found to be identical by restriction mapping. The other two plasmids were not further examined. The insert from the first clone, designated pHfIX1, was further mapped by restriction endonuclease digestion. Sites for cleavage and end-labeling were chosen from the detailed restriction map, and both 5' and 3' labeling methods were used. The coding strand was used to number the DNA sequence which is presented in the same orientation as the ampicillin-resistance gene of pBR322. The insert has been described above.

In accordance with the subject invention, DNA sequences are provided for hybridization with pro-factor IX, factor IX, factor IX$_a$, and activation peptide, and for DNA and RNA fragments which can be used in the detection of mutations or other genetic deficiencies concerned with factor IX. The sequences can be used in diagnosing blood clotting deficiencies, such as hemophilia, particularly hemophilia B. By lysing cells as described above and screening the DNA with fragments according to the subject invention, mutations in the factor IX gene may be determined.

Although the foregoing invention has been described in some detail by way of illustration and example for purposes of clarity of understanding, it will be obvious that certain changes and modifications may be practiced within the scope of the appended claims.

What is claimed is:

1. An isolated DNA sequence consisting essentially of a sequence encoding human factor IX.

2. The isolated DNA sequence of claim 1 wherein said DNA is cDNA.

3. The isolated DNA sequence of claim 1 where said DNA is closed chromosomal DNA.

4. An isolated DNA sequence encoding the amino acid sequence of the FIGURE from amino acid +1(Tyr) through amino acid +416 (Thr).

5. An isolated DNA sequence encoding the amino acid sequence of the FIGURE from amino acid −46 (Met) to amino acid +416 (Thr).

6. An isolated DNA sequence encoding the sequence of the FIGURE from base 150 to base 1397, wherein said sequence codes for human factor IX.

7. An isolated DNA sequence encoding the sequence of the FIGURE from base 12 to base 1397, wherein said sequence codes for the precursor of human factor IX.

8. A polynucleotide having a length of at least 14 nucleotides and not more than 3,000 nucleotides, wherein said polynucleotide is the same sequence as or complementary to a DNA base sequence encoding human factor IX, wherein said polynucleotide is free of other polynucleotide sequences of human origin that do not exist in the DNA sequence encoding human factor IX.

9. A polynucleotide according to claim 8 wherein the polynucleotide is joined to a label moiety to provide a means for its direction.

10. A polynucleotide according to claim 9 wherein the label is a radionuclide.

11. A method of detection in a human cell or cells, of a mutation in the gene encoding factor IX or the 5' flanking sequence of up to 1500 bases thereof, said method comprising:

combining DNA from said human cell or cells with a polynucleotide having a length of at least 14 nucleotides and not more than 3,000 nucleotides, wherein said polynucleotide is the same sequence as, or is complementary to a DNA sequence encoding human factor IX, under hybridizing conditions of predetermined stringency; wherein said polynucleotide is free of other polynucleotide sequence of human origin that do not exist in the DNA sequence encoding human factor IX;

washing the combined DNA and said polynucleotide; and detecting duplex formation as diagnostic of the presence of genetic mutation.

12. A method according to claim 11, wherein said polynucleotide is joined to a label moiety to provide a means for its detection.

13. A method according to claim 12, wherein said label moiety is a radionuclide.

14. A method according to claim 13, wherein said DNA from said cell or cells is bound to a solid support.

15. A plasmid cloning vector comprising a DNA sequence encoding human factor IX.

16. The plasmid cloning vector of claim 15 wherein said DNA sequence comprises cDNA.

17. The plasmid cloning vector of claim 15 wherein said DNA sequence comprises cloned chromosomal DNA.

18. The plasmid cloning vector of claim 15, wherein said DNA sequence encodes the amino acid sequence of the FIGURE from amino acid +1(Tyr) to amino acid +416(Thr).

19. The plasmid cloning vector of claim 15 wherein said DNA sequence encodes the amino acid sequence of the FIGURE from amino acid (−36(Met) to amino acid +146(Thr).

20. The plasmid cloning vector of claim 15 wherein said DNA sequence comprises the nucleotide sequence of the FIGURE from base 150 to base 1397, which nucleotide sequence codes for human factor IX.

21. The plasmid cloning vector of claim 15 wherein said DNA sequence comprises the nucleotide sequence of the FIGURE from base 12 to base 1397, which sequence codes for the precursor of human factor IX.

22. The plasmid cloning vector of claim 15 further comprising a transcriptional promoter operably linked to the DNA sequence.

23. An isolated DNA sequence consisting essentially of a sequence encoding a human factor IX immediately preceded by a leader sequence.

* * * * *

UNITED STATES PATENT AND TRADEMARK OFFICE
CERTIFICATE OF CORRECTION

PATENT NO. : 4,994,371
DATED : February 19, 1991
INVENTOR(S) : Earl W. Davie; Kotoku Kurachi It is certified that error appears in the above-identified patent and that said Letters Patent is hereby corrected as shown below:

On the title page, and in col. 1, lines 2-3 change the title to read--rDNA PREPARATION OF CHRISTMAS FACTOR AND USE OF DNA SEQUENCES--.

On the cover page, please include Washington Research Foundation, Seattle, Washington as assignee.

In column 10, claim 3, line 16, please delete "closed" and substitute therefor --cloned--.

In column 10, claim 9, line 39, please delete "direction" and substitute therefor --detection--.

In column 10, claim 14, line 65, please delete "13" and substitute therefor --11--.

In column 11, claim 19, line 14, please delete "(-36(Met)" and substitute therefor -- -46(Met) --.

In column 11, claim 19, line 15, please delete "+146(Thr)" and substitute therefor -- +416(Thr) --.

Signed and Sealed this

First Day of December, 1992

Attest:

DOUGLAS B. COMER

Attesting Officer      Acting Commissioner of Patents and Trademarks